(12) United States Patent
Borca et al.

(10) Patent No.: US 8,063,195 B2
(45) Date of Patent: Nov. 22, 2011

(54) MUTATIONS IN A TOLL-LIKE RECEPTOR MOTIF IN THE NS4B OF CLASSICAL SWINE FEVER VIRUS STRAIN BRESCIA INFLUENCES VIRULENCE IN SWINE

(75) Inventors: Manuel V. Borca, Westbrook, CT (US); James J. Zhu, Niantic, CT (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/454,766

(22) Filed: May 22, 2009

(65) Prior Publication Data

US 2010/0297175 A1    Nov. 25, 2010

(51) Int. Cl.
 *C12N 15/11* (2006.01)
 *A61K 48/00* (2006.01)
(52) U.S. Cl. .................. 536/23.72; 424/93.1; 435/169.1
(58) Field of Classification Search .................. None
 See application file for complete search history.

(56) References Cited

U.S. PATENT DOCUMENTS 5,925,360 A * 7/1999 Meyers et al. ............. 424/220.1
6,180,109 B1 * 1/2001 Moormann et al. ....... 424/204.1

FOREIGN PATENT DOCUMENTS

WO    WO 9100352 A  *  1/1991

OTHER PUBLICATIONS

Risatti et al. J. Virol. 2005, vol. 79, No. 6, pp. 3787-3796.*

* cited by examiner

*Primary Examiner* — Bao Li
(74) *Attorney, Agent, or Firm* — John D. Fado; Evelyn M. Rabin; Gail E. Poulos

(57) ABSTRACT

NS4B is one of the non-structural proteins of classical swine fever virus. By using functional genetics, we have discovered, in the predicted amino acid sequence of NS4B of CSFV strain Brescia, a motif that resembles those found in the toll-like receptor (TLR) proteins, a group of host cell proteins involved in the development of anti-viral mechanisms. We have located the TLR motif in two groups of amino acid triplets at amino acid positions 2531-3 (residues IYK) and 2566-8 (residues VGI) of the CSFV NS4B glycoprotein. We have constructed a recombinant CSFV (derived from an infectious clone containing the genetic information of the highly virulent strain Brescia) containing amino acid substitutions in the three amino acid residues at positions 2566, 2567 and 2568, where the VGI triplet has been replaced by an AAA triplet inside the NS4B glycoprotein. The obtained virus, named NS4B-VGIv, was completely attenuated in swine, showing a limited ability in spreading during the infection in vivo. Although attenuated, NS4B-VGIv efficiently protected swine from challenge with virulent BICv at 3 and 28 days post-infection.

11 Claims, 2 Drawing Sheets
(1 of 2 Drawing Sheet(s) Filed in Color)

Fig.1

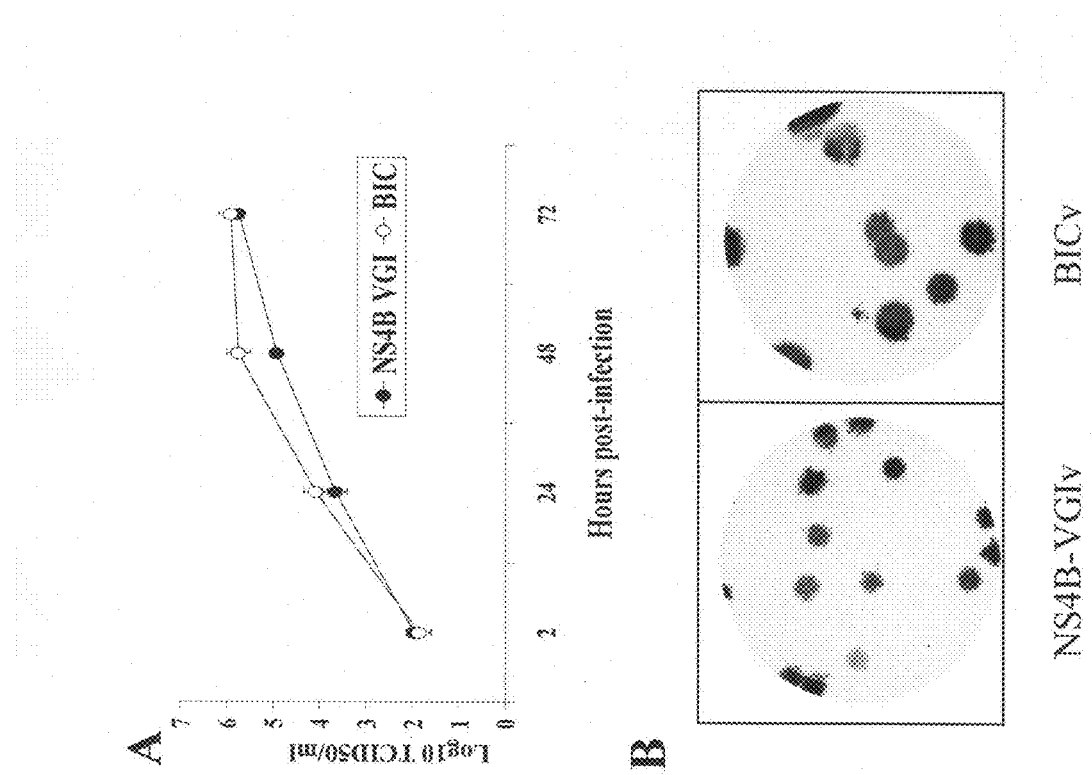

MUTATIONS IN A TOLL-LIKE RECEPTOR MOTIF IN THE NS4B OF CLASSICAL SWINE FEVER VIRUS STRAIN BRESCIA INFLUENCES VIRULENCE IN SWINE

BACKGROUND OF THE INVENTION

1. Field of the Invention

This invention relates to the characterization of the role that a toll-like receptor (TLR) motif in the amino acid sequence of the non-structural protein NS4B of highly virulent Classical Swine Fever Virus (CSFV) strain Brescia plays during infection in the natural host and to the utilization of a strategy for altering CSFV virulence by replacing the TLR motif with a different amino acid triplet to obtain an attenuated recombinant virus, NS4B-VGIv, which protects swine from challenge with virulent BICv.

2. Description of the Relevant Art

Classical swine fever (CSF) is a highly contagious disease of swine. The etiological agent, CSF virus (CSFV), is a small, enveloped virus with a positive, single-stranded RNA genome and, along with Bovine Viral Diarrhea Virus (BVDV) and Border Disease Virus (BDV), is classified as a member of the genus *Pestivirus* within the family Flaviridae (Becher et al. 2003. *Virology* 311: 96-104). The 12.5 kb CSFV genome contains a single open reading frame that encodes a 3898-amino-acid polyprotein and ultimately yields 11 to 12 final cleavage products ($NH_2$-Npro-C-$E^{rns}$-E1-E2-p7-NS2-NS3-NS4A-NS4B-NS5A-NS5B-COOH) through co- and post-translational processing of the polyprotein by cellular and viral proteases (Rice, C. M. 1996. In: *Fundamental Virology*, 3rd edition, Knipe et al., eds., Lippincott Raven, Philadelphia, Pa., pages 931-959).

The non-structural glycoprotein 4B (NS4B) of CSFV is one of the non-structural proteins of classical swine fever virus. NS4B has previously been poorly characterized in terms of its functionality. Using genomic analyses we have found that NS4B possesses a specific motif that is found in proteins of the Toll-Like Receptor (TLR) family. In general, TLRs are pattern-recognition receptors that recognize structurally conserved molecules derived from microbes. Their expression is readily modulated in response to pathogens and plays an important role in mounting the host immune response. Although the function of natural ligands of swine TLRs is still under study, these molecules are highly conserved within the Vertebrata, suggesting activities similar to other published vertebrate TLRs and their ligands.

Strategies for controlling disease in the event of a CSFV outbreak include the production of rationally designed live attenuated vaccine CSFV strains. Here, we report the effects of modification of the TLR of NS4B on viral infectivity and virulence in swine.

SUMMARY OF THE INVENTION

We have discovered that the CSFV non-structural glycoprotein NS4B possesses a specific motif that is found in proteins of the Toll-like Receptor (TLR) family and that modification of sites within the TLR motif results in CSFV having novel virulence determinants.

In accordance with this discovery, it is an object of the invention to provide a recombinant CSFV comprising DNA encoding a modified CSFV NS4B glycoprotein wherein specific sites within NS4B have been mutated resulting in an alteration in the site, i.e., the formerly valine-glycine-isoleucine (VGI) peptide being altered and replaced by an alanine triplet (AAA).

It is also an object of the invention to provide an isolated polynucleotide molecule comprising a genetically modified DNA sequence encoding a genetically modified infectious RNA molecule encoding a genetically modified CSFV. The CSFV is genetically modified such that when it infects a porcine animal it is unable to produce CSFV in the animal and it is able to elicit an effective immunoprotective response against infection by a CSFV in the animal. Mutated sequences contain a modified peptide in the TLR motif of NS4B that renders the encoded CSFV attenuated and able to elicit an effective immunoprotective response against infection by a CSFV in the animal.

It is additionally an object of the invention to provide an isolated infectious RNA molecule encoded by the isolated polynucleotide molecule recited above, and isolated infectious RNA molecules homologous thereto, which isolated infectious RNA molecules each encode a genetically modified CSFV, disabled in its ability to produce CSF.

An added object of the invention is to provide immunogenic compositions comprising a viable recombinant CSFV comprising a modified CSFV NS4B non-structural glycoprotein displaying a peptide sequence in the TLR-region of NS4B which is different from that of the non-mutated NS4B glycoprotein.

An additional object of the invention is to provide a rationally designed live attenuated CSFV vaccine which lessens severity of CSF disease when challenged with virulent Brescia CSFV wherein said vaccine comprises an altered TLR motif within the NS4B non-structural glycoprotein as compared to that of the infectious, non-mutated virus.

Another object of the invention is to provide a rationally designed live attenuated CSFV vaccine effective to protect an animal from clinical CSF disease when challenged with virulent Brescia CSFV wherein said vaccine comprises an altered TLR motif within the NS4B non-structural glycoprotein as compared to that of the infectious, non-mutated virus.

Yet another object of the invention is to provide a method for protecting an animal against CSF by administering an effective amount of the rationally designed live attenuated CSFV vaccine.

An additional object of the invention is to provide a method for delaying onset or severity of CSF in an animal by administering an effective amount of the rationally designed live attenuated CSFV vaccine.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 1 depicts infectious RNA that was in vitro transcribed from full-length ICs of the CSFV Brescia containing mutations at the desired amino acid positions and used to transfect SK6 cells. Mutants referred to as NS4B-IYK and NS4B-VGI and double mutant NS4B-IYK/VGI contain their putative TLR-like motifs substituted by alanine residues.

FIG. 2A depicts in vitro growth characteristics of mutant virus NS4B-VGIv evaluated relative to parental BICv in a multistep growth curve. Relative virus yield is final point virus yield as proportion of final end point (72 hours post-infection) virus yield of parental BICv. Primary swine macrophage cell cultures were infected at a MOI of 0.01 $TCID_{50}$/ cell. Virus was adsorbed for 1 h (time zero), and samples were collected at times post-infection through 72 h. NS4B-VGIv exhibited growth characteristics practically indistinguishable from BICv, exhibiting similar titers in the final virus yield. FIG. 2B depicts the results of testing NS4B-VGIv for their plaque size in SK6 cells. NS4B-VGIv exhibited a slight reduction (1.07 cm, with a SD of 0.06) in plaque size relative to BICv (1.79 cm, with a SD of 0.17).

DETAILED DESCRIPTION OF THE INVENTION

We have located the TLR motif in two groups of amino acid triplets at amino acid positions 2531-3, residues isoleucine-tyrosine-lysine (IYK), and 2566-8, residues valine-glycine-isoleucine (VGI), of the CSFV polyprotein. Based on that information, we have constructed a recombinant CSFV named NS4B-VGIv. The NS4B-VGIv virus was derived from an infectious clone containing the genetic information of the highly virulent strain Brescia and contains amino acid substitutions in three amino acid residues, namely, CSFV residue positions 2566, 2567 and 2568, where the VGI triplet has been replaced by an alanine triplet (AAA) inside the NS4B polyprotein. The recombinant NS4B-VGIv virus has been shown to grow in vitro (both in swine macrophage primary cell cultures and in SK6 cell cultures) almost indistinguishably from the parental CSFV. Importantly, NS4B-VGIv is completely attenuated when inoculated intranasally in swine. NS4B-VGIv replicates only locally (in the tonsil area) at very low titers when compared to the parental Brescia virus, and barely generates a generalized infection (i.e., reaching secondary target organs). Additionally, animals infected with NS4B-VGIv were completely protected against virulent challenge with Brescia virus both at 3 and 28 days post-vaccination. Thus, NS4B-VGIv serves as a candidate vaccine virus having advantages over classic live attenuated strains, since the molecular basis of its attenuation is known.

Production and manipulation of the isolated polynucleotide molecules described herein are within the skill in the art and can be carried out according to recombinant techniques described, among other places, in Sambrook et al. 1989. *Molecular Cloning: A Laboratory Manual,* 2d ed., Cold Spring Harbor Laboratory Press, Cold Spring Harbor, N.Y. and Innis et al. (eds). 1995. *PCR Strategies,* Academic Press, Inc., San Diego, which are incorporated herein by reference.

The subject invention provides isolated polynucleotide molecules comprising genetically modified DNA sequences that encode genetically modified infectious RNA molecules that encode genetically modified Classical Swine Fever Viruses (CSFVs).

In particular, the subject invention provides an isolated polynucleotide molecule comprising a genetically modified DNA sequence encoding a genetically modified infectious RNA molecule that encodes a genetically modified CSFV, VGIv, wherein said DNA sequence is SEQ ID NO:1 or sequences homologous thereto encoding the mutated virus. Said DNA sequences encode infectious RNA molecules that are the RNA genomes of the NS4B-VGIv virus, the candidate vaccine virus.

It is understood that terms herein referring to nucleic acid molecules such as "isolated polynucleotide molecule" and "nucleotide sequence include both DNA and RNA molecules and include both single-stranded and double-stranded molecules whether it is natural or synthetic origin.

For example, SEQ ID NO:1 is a DNA sequence corresponding to the genetically modified RNA genome of a genetically modified CSFV, VGIv. Thus, a DNA sequence complementary to the DNA sequence set forth in SEQ ID NO:1 is a template for, i.e. is complementary to or "encodes", the RNA genome of the CSF virus (i.e., RNA that encodes the CSFV).

Furthermore, when reference is made herein to sequences homologous to a sequence in the Sequence Listing, it is to be understood that sequences are homologous to a sequence corresponding to the sequence in the Sequence Listing and to a sequence complementary to the sequence in the Sequence Listing.

An "infectious RNA molecule", for purposes of the present invention, is an RNA molecule that encodes the necessary elements for viral replication, transcription, and translation into a functional virion in a suitable host cell, provided, if necessary, with a peptide or peptides that compensate for any genetic modifications, e.g. sequence deletions, in the RNA molecule.

An "isolated infectious RNA molecule" refers to a composition of matter comprising the aforementioned infectious RNA molecule purified to any detectable degree from its naturally occurring state, if such RNA molecule does indeed occur in nature. Likewise, an "isolated polynucleotide molecule" refers to a composition of matter comprising a polynucleotide molecule of the present invention purified to any detectable degree from its naturally occurring state, if any.

For purposes of the present invention, two DNA sequences are substantially homologous when at least 80% (preferably at least 85% and most preferably 90%) of the nucleotides match over the defined length of the sequence using algorithms such as CLUSTRAL or PILEUP. Sequences that are substantially homologous can be identified in a Southern hybridization experiment under stringent conditions as is known in the art. See, for example, Sambrook et al., supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Thus, isolated sequences that encode a modified CSFV non-structural protein NS4B and which hybridize under stringent conditions, as described herein, to the modified CSFV NS4B sequences disclosed herein or to fragments thereof, are encompassed by the present invention. Fragments of a nucleotide sequence that are useful as hybridization probes may not encode fragment proteins retaining biological activity.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of the modified CSFV non-structural NS4B protein of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, a modified CSFV NS4B non-structural protein activity as described herein. Such variants may result from, for example, genetic polymorphism or from human manipulation. Biologically active variants of a modified CSFV NS4B non-structural protein of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired modified CSFV non-structural protein, NS4B, activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of modified CSFV NS4B non-structural protein activity, can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is furthermore to be understood that the isolated polynucleotide molecules and the isolated RNA molecules of the present invention include both synthetic molecules and molecules obtained through recombinant techniques, such as by in vitro cloning and transcription.

As used herein, the term "CSF" encompasses disease symptoms in swine caused by a CSFV infection. Examples of such symptoms include, but are not limited to, anorexia, depression, fever, purple skin discoloration, staggering gait, diarrhea and cough. As used herein, a CSFV that is "unable to produce CSF" refers to a virus that can infect a pig, but which does not produce any disease symptoms normally associated with a CSF infection in the pig, or produces such symptoms, but to a lesser degree, or produces a fewer number of such symptoms, or both.

The terms "porcine" and "swine" are used interchangeably herein and refer to any animal that is a member of the family Suidae such as, for example, a pig. "Mammals" include any warm-blooded vertebrates of the Mammalia class, including humans.

The terms "classical swine fever virus" and "CSFV", as used herein, unless otherwise indicated, mean any strain of CSF viruses.

The term "open reading frame", or "ORF", as used herein, means the minimal nucleotide sequence required to encode a particular CSFV protein without an intervening stop codon.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present invention can be transformed or transfected. "Suitable host cells" for transfection with such RNA molecules, isolated polynucleotide molecules, or viral vectors, include mammalian, particularly porcine cells, and are described in further detail below.

A "functional virion" is a virus particle that is able to enter a cell capable of hosting a CSFV, and express genes of its particular RNA genome (either an unmodified genome or a genetically modified genome as described herein) within the cell. Cells capable of hosting a CSFV include swine kidney cells (SK6) and primary porcine macrophage cell cultures. Other mammalian cells, especially other porcine cells, may also serve as suitable host cells for CSF virions.

The isolated polynucleotide molecules of the present invention encode CSF viruses that can be used to prepare live attenuated vaccines using art-recognized methods for protecting swine from infection by a CSFV, as described in further detail below. Furthermore, these isolated polynucleotide molecules are useful because they can be mutated using molecular biology techniques to encode genetically-modified CSF viruses useful, inter alia, as vaccines for protecting swine from CSF infection. Such genetically-modified CSF viruses, as well as vaccines comprising them, are described in further detail below.

Accordingly, the subject invention further provides a method for making a genetically modified CSFV, which method comprises mutating the DNA sequence encoding an infectious RNA molecule which encodes the CSFV as described above, and expressing the genetically modified CSFV using a suitable expression system. A CSFV, either wild-type or genetically modified, can be expressed from an isolated polynucleotide molecule using suitable expression systems generally known in the art, examples of which are described in this application. For example, the isolated polynucleotide molecule can be in the form of a plasmid capable of expressing the encoded virus in a suitable host cell in vitro.

The term "genetically modified", as used herein and unless otherwise indicated, means genetically mutated, i.e. having one or more nucleotides replaced, deleted and/or added. Polynucleotide molecules can be genetically mutated using recombinant techniques known to those of ordinary skill in the art, including by site-directed mutagenesis, or by random mutagenesis such as by exposure to chemical mutagens or to radiation, as known in the art.

The subject invention further provides an isolated polynucleotide molecule comprising a DNA sequence encoding an infectious RNA molecule which encodes a genetically modified CSFV that is unable to produce CSF in a porcine animal, wherein the DNA sequence encoding the infectious RNA molecule encoding said modified CSFV is SEQ ID NO:1 or sequences homologous thereto, contains one or more mutations that genetically disable the encoded CSFV in its ability to produce CSF. "Genetically disabled" means that the CSFV is unable to produce CSF in a swine animal infected therewith.

In one embodiment, the genetically modified CSFV disabled in its ability to cause CSF is able to elicit an effective immunoprotective response against infection by a CSFV in a swine animal. Accordingly, the subject invention also provides an isolated polynucleotide molecule comprising a DNA sequence encoding an infectious RNA molecule which encodes a CSFV that is genetically modified such that when it infects a porcine animal it: a) is unable to produce CSF in the animal, and b) is able to elicit an effective immunoprotective response against infection by a CSFV in the animal, wherein the DNA sequence encoding said modified CSFV is SEQ ID NO:1 or sequences homologous thereto, contains one or more mutations that genetically disable the encoded CSFV in its ability to produce CSF.

The term "immune response" for purposes of this invention means the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

An "antigenic epitope" is, unless otherwise indicated, a molecule that is able to elicit an immune response in a particular animal or species. Antigenic epitopes are proteinaceous molecules, i.e. polypeptide sequences, optionally comprising non-protein groups such as carbohydrate moieties and/or lipid moieties.

The genetically modified CSF viruses encoded by the above-described isolated polynucleotide molecules are, in one embodiment, able to elicit an effective immunoprotective response against infection by a CSFV. Such genetically modified CSF viruses are preferably able to elicit an effective immunoprotective response against any strain of CSF viruses.

In one embodiment, the mutation or mutations in the isolated polynucleotide molecule encoding the genetically disabled CSFV are non-silent and occur in one or more open reading frames of the nucleotide sequence encoding the CSFV.

As used herein, unless otherwise indicated, "coding regions" refer to those sequences of RNA from which CSFV proteins are expressed, and also refer to cDNA that encodes such RNA sequences. Likewise, "ORFs" refer both to RNA sequences that encode CSFV proteins and to cDNA sequence encoding such RNA sequences.

Determining suitable locations for a mutation or mutations that will encode a CSFV that is genetically disabled so that it is unable to produce CSF yet remains able to elicit an effective immunoprotective response against infection by a CSFV can be made based on SEQ ID NO:1 provided herein. One of ordinary skill can refer to the sequence of the infectious cDNA clone of CSFV provided by this invention, make sequence changes which will result in a mutation altering the TLR motif of the NS4B glycoprotein, and test the viruses encoded thereby both for their ability to produce CSF in swine, and to elicit an effective immunoprotective response against infection by a CSFV. In so doing, one of ordinary skill can refer to techniques known in the art and also those described and/or exemplified herein.

For example, an ORF of the sequence encoding the infectious RNA molecule encoding the CSFV can be mutated and the resulting genetically modified CSFV tested for its ability to cause CSF.

Antigenic epitopes that are detectable, and the sequences that encode them, are known in the art. Techniques for detecting such antigenic epitopes are also known in the art and include serological detection of antibody specific to the heterologous antigenic epitope by means of, for example, Western blot, ELISA, or fluorescently labeled antibodies capable of binding to the antibodies specific to the heterologous antigenic epitope. Techniques for serological detection useful in practicing the present invention can be found in texts recognized in the art, such as Coligan, J. E., et al. (eds), 1998, *Current Protocols in Immunology*, John Willey & Sons, Inc., which is hereby incorporated by reference in its entirety. Alternatively, the antigenic epitope itself can be detected by, for example, contacting samples that potentially comprise the antigenic epitope with fluorescently-labeled antibodies or radioactively-labeled antibodies that specifically bind to the antigenic epitopes.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., *Remington's Pharmaceutical Science,* 18th ed., 1990, Mack Publishing, which is incorporated herein by reference.

Vaccines of the present invention can further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines.

Vaccines of the present invention can optionally be formulated for sustained release of the virus, infectious RNA molecule, plasmid, or viral vector of the present invention. Examples of such sustained release formulations include virus, infectious RNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including Domb et al. 1992. *Polymers for Advanced Technologies* 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in: *Drugs and the Pharmaceutical Sciences,* Vol. 45, M. Dekker, NY, which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of virus, plasmid, or viral vector. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, infectious RNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 g to about 100 mg, more preferably from about 1 µg to about 10 mg, even more preferably from about 10 µg to about 1 mg. The dose amount of an infectious RNA molecule of the present invention in a vaccine of the present invention preferably ranges from about 0.1 µg to about 100 mg, more preferably from about 1 µg to about 10 mg, even more preferably from about 10 µg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

EXAMPLES

Having now generally described this invention, the same will be better understood by reference to certain specific examples, which are included herein only to further illustrate the invention and are not intended to limit the scope of the invention as defined by the claims.

Example 1

Viruses and Cell Cultures

Swine kidney cells (SK6) (Terpstra et al., supra) free of Bovine Viral Diarrhea Virus (BVDV) were cultured in Dulbecco's Minimal Essential Medium (DMEM, GIBCO, Grand Island, N.Y.) with 10% fetal calf serum (FCS, Atlas Biologicals, Fort Collins, Colo.). CSFV Brescia strain (obtained from the Animal and Plant Health Inspection Service, Plum Island Animal Disease Center) was propagated in SK6 cells and used for an infectious cDNA clone (Risatti et al. 2005a, supra). Growth kinetics were assessed on primary swine macrophage cell cultures prepared as described by Zsak et al. (1996. *J. Virol.* 70: 8865-8871). Titration of CSFV from clinical samples was performed using SK6 cells in 96-well plates (Costar, Cambridge, Mass.). Viral infectivity was detected, after 4 days in culture, by an immunoperoxidase assay using the CSFV monoclonal antibodies WH303 (Edwards et al. 1991. *Vet. Microbiol.* 29:101-108) and the Vectastain ABC kit (Vector Laboratories, Burlingame, Calif.). Titers were calculated using the method of Reed and Muench (1938. *American J. Hygiene* 27: 493-497) and expressed as $TCID_{50}$/ml. As performed, test sensitivity was ≧log 10 1.8 TCID50/ml. Plaque assays were performed using SK6 cells in 6-well plates (Costar). SK6 monolayers were infected, overlaid with 0.5% agarose and incubated at 37° C. for 3 days. Plates were fixed with 50% (vol/vol) ethanol-acetone and stained by immunohistochemistry with mAb WH303 (Risatti et al. 2003. *J. Clin. Microbiol.* 41: 500-505).

Example 2

Construction of CSFV NS4B Mutants

A full-length infectious clone of the virulent Brescia isolate (pBIC) (Risatti et al. 2005a, supra) was used as a template in which putative TLR motifs IYK and VGI at amino acid positions 2531-2533 and 2566-2568 of the CSFV polypeptide, respectively, were replaced by AAA triplets. Mutations were introduced by site-directed mutagenesis using the QuickChange XL Site-Directed Mutagenesis kit (Stratagene, Cedar Creek, Tex.) performed per manufacturer's instructions and using the following primers (only forward primer sequences are shown); IYK mutant: GTCATACTGAGTAC-CGCAGCC GCCGCAACCTACCTATCAATCAGG (SEQ ID NO:3); VGI mutant: TCACAAAACCCA GTATCTGCG-GCTGCAGCGGTCATGCTAGGGGTG (SEQ ID NO:4).

Example 3

In Vitro Rescue of CSFV Brescia and NS4B Mutants

Full-length genomic clones were linearized with SrfI and in vitro transcribed using the T7 Megascript system (Ambion, Austin, Tex.). RNA was precipitated with LiCl and transfected into SK6 cells by electroporation at 500 volts, 720 ohms, 100 watts with a BTX 630 electroporator (BTX, San Diego, Calif.). Cells were seeded in 12-well plates and incubated for 4 days at 37° C. and 5% $CO_2$. Virus was detected by immune-peroxidase staining as described above, and stocks of rescued viruses were stored at −70° C.

Figure 1:
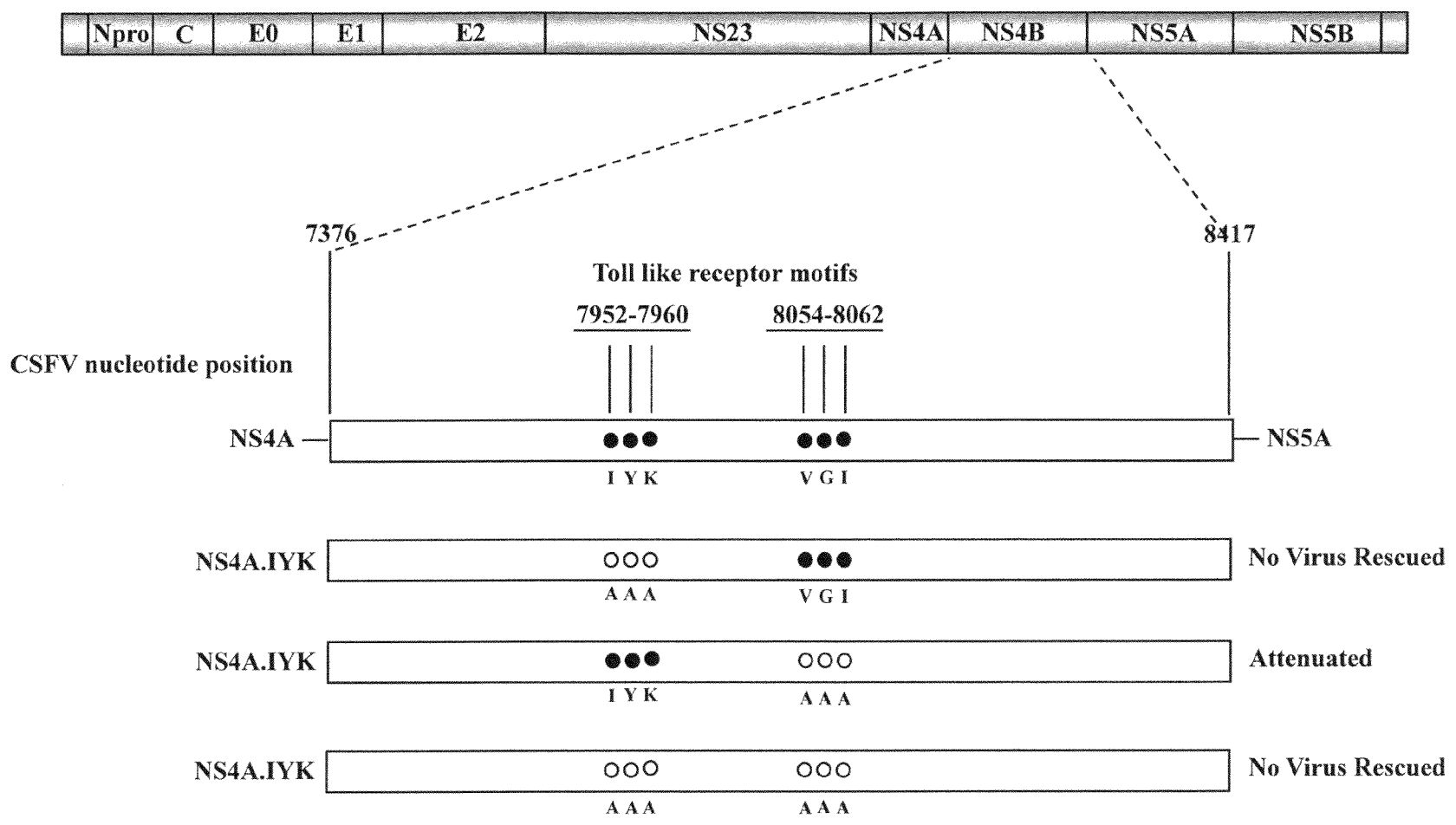

Infectious RNA was in vitro transcribed from full-length infectious clones of the CSFV Brescia strain containing mutations at the desired amino acid positions (FIG. 1) and used to transfect SK6 cells. Mutants referred to as NS4B-IYK and NS4B-VGI and double mutant NS4B-IYK/VGI contain their putative TLR-like motifs substituted by alanine residues (FIG. 1). Viruses were rescued from transfected cells by day 4 post-transfection. After three independent transfection procedures, NS4B-IYK and NS4B-IYK/VGI constructs did not produce infectious viruses. NS4B-IYK and NS4B-IYK/VGI RNA transcripts used in transfections were completely sequenced in order to ensure fidelity during the in vitro transcription process. Nucleotide sequence of the rescued virus genome was identical to parental DNA plasmids, confirming that only mutations at predicted motif sites were reflected in rescued virus.

Example 4

DNA Sequencing and Analysis

Full-length infectious clones and in vitro rescued virus were completely sequenced with CSFV specific primers by the dideoxynucleotide chain-termination method (Sanger et al. 1977. *Proc. Natl. Acad. Sci. USA* 74: 5463-5467). Viruses recovered from infected animals were sequenced in the mutated area. Sequencing reactions were prepared with the Dye Terminator Cycle Sequencing Kit (Applied Biosystems, Foster City, Calif.). Reaction products were sequenced on a PRISM 3730xl automated DNA Sequencer (Applied Biosystems). Sequence data were assembled with Squencher® (Genes Codes Corporation, Ann Arbor, Mich.). The final DNA consensus sequence represented, on average, five redundancies at each base position.

The DNA sequence encoding a modified CSFV NSb4-VGIv is identified by SEQ ID NO:1.

Example 5

In Vitro and In Vivo Analysis of NS4B-VGIv Mutants

In vitro growth characteristics of mutant virus NS4B-VGIv was evaluated relative to parental BICv in a multistep growth curve (FIG. 2A). Primary porcine macrophage cell cultures were infected at a multiplicity of infection (MOI) of 0.01 $TCID_{50}$ per cell. Virus was adsorbed for 1 h (time zero), and samples were collected at times post-infection through 72 h.

NS4B-VIGv exhibited growth characteristics practically indistinguishable from BICv, exhibiting similar titers in the final virus yield (FIG. 2A). Additionally, when NS4B-VIGv was tested for their plaque size in SK6 cells, NS4B-VIGv exhibited a slight reduction (1.07 cm, with a SD of 0.06) in plaque size relative to BICv (1.79 cm, with a SD of 0.17) (FIG. 2B).

NS4B-VIGv mutant virus was initially screened for its virulence phenotype in swine relative to virulent Brescia virus. Swine used in all animal studies were 10 to 12 weeks old, forty-pound commercial breed pigs inoculated intranasally with $10^5$ $TCID_{50}$ of VGI mutant or wild-type virus (Table 1). For screening, 14 pigs were randomly allocated into 2 groups of 8 and 6 animals each, and pigs in each group were inoculated with NS4B-VGIv or BICv, respectively. Clinical signs (anorexia, depression, fever, purple skin discoloration, staggering gait, diarrhea and cough) and changes in body temperature were recorded daily throughout the experiment and scored as previously described (Mittelholzer et al. 2000. *Vet. Microbiol.* 74: 293-308).

TABLE 1

Swine survival and fever response following infection with CSFV NS4B-VGIv mutants and parental BICv.

| Virus | No. survivors/ Total | Mean time to death (days ± SD) | Fever No. of days to onset (days ± SD) | Duration (days ± SD) |
|---|---|---|---|---|
| NS4B-VGI | 8/8 | — | — | — |
| BICv | 6/6 | 11 (0.82) | 3 (0) | 6.75 (1.71) |

SD: Standard Deviation

While BICv exhibited a characteristic virulent phenotype, animals infected with NS4B-VGIv survived the infection and remained normal throughout the observation period (21 days). All animals infected with BICv presented clinical signs of CSF starting 4 to 6 DPI. White blood cell and platelet counts dropped by 4 to 6 DPI in animals inoculated with BICv and kept declining until death, while a transient decrease was observed in animals inoculated with NS4B-VGI (data not shown).

To assess the effect of the NS4B-VGIv mutation on virus shedding and distribution in different organs during infection, pigs were randomly allocated into 3 groups of 9 animals each and intranasally inoculated (see above) with NS4B-VGIv or BICv. One pig per group was sacrificed at 6 hr and 1 2, 4, 6, 8 and 12 DPI. Blood, nasal swabs and tonsil scraping samples were obtained from pigs at necropsy. Tissue samples (tonsil, mandibular lymph node, spleen and kidney) were snap-frozen in liquid nitrogen for subsequent virus titration. The remaining 2 pigs in each room were monitored to check for appearance of clinical signs during a 21-day period.

The capability of NS4B-VGIv to establish a systemic infection in intranasally inoculated animals was compared with that of virulent parental virus BICv. Viremia in NS4B-VGIv-inoculated animals was transient (Tables 2 and 3) and significantly reduced by $10^4$ to $10^5$ from that observed in BICv infected swine. A similar pattern was observed for nasal and tonsil samples (Table 2). In all cases, complete nucleotide sequences of NS4B protein from viruses recovered from infected animals were identical to those of stock viruses used for inoculation (data not shown).

TABLE 2

Titers of virus in clinical samples after intranasal inoculation with mutant NS4B-VGIv and parental BICv.

| | | Viral Titers ($TCID_{50}$/ml) | | |
|---|---|---|---|---|
| Virus | DPI | Blood | Nasal Swabs | Tonsil Scrapes |
| NS4B-VGIv | 4 | 0/4[a] | 1/4 (1.9) | 0/4 |
| | 6 | 3/4 (2.2) | 1/4 (2.4) | 0/4 |
| | 8 | 1/4 (2.0) | 0/4 | 1/4 (1.90) |
| | 12 | 0/4 | 0/4 | 0/4 |
| BICv | 4 | 4/4 (4.5) | 0/4 | 4/4 (2.0) |
| | 6 | 4/4 (7.2) | 4/4 (4.5) | 4/4 (4.1) |
| | 8 | 4/4 (7.6) | 4/4 (5.0) | 4/4 (4.8) |
| | 12 | D[b] | D | D |

[a]Number of animals with virus titers/number of total inoculated animals in the group.
[b]D, animals in this group were all dead by this time point.

Titers measured in those tissue samples are shown in Table 3. In vivo replication of NS4B-VGIv was transient in tonsils with titers reduced up to $10^2$ to $10^5$, depending on the time post-infection, relative to those of BICv. Differences between NS4B-VGIv and BICv virus titers were also observed in mandibular lymph nodes (MLN) and retropharyngeal lymph nodes (RPLN), and no mutant virus was detected in spleen and kidney, indicating a severely limited capability of NS4B-VGIv to spread within the host.

TABLE 3

Titers of virus in tissues after intranasal inoculation with mutant NS4B-VGIv and parental BICv.

| | | Viral Titers ($TCID_{50}$ %/ml) | | | | | |
|---|---|---|---|---|---|---|---|
| Virus | DPI | Tonsil | MLN | RPLN | Spleen | Kidney | Blood |
| NS4B-VGIv | 1 | neg* | neg | neg | neg | neg | neg |
| | 2 | neg | neg | neg | neg | neg | neg |
| | 3 | neg | 1.97 | 2.1 | neg | neg | neg |
| | 4 | neg | 1.97 | 2.2 | neg | neg | neg |
| | 7 | n.d. | neg | 3.2 | neg | neg | neg |
| | 9 | neg | neg | neg | neg | neg | neg |

TABLE 3-continued

Titers of virus in tissues after intranasal inoculation with mutant NS4B-VGIv and parental BICv.

| | | Viral Titers ($TCID_{50}$ %/ml) | | | | | |
|---|---|---|---|---|---|---|---|
| Virus | DPI | Tonsil | MLN | RPLN | Spleen | Kidney | Blood |
| BICv | 1 | neg | neg | neg | neg | neg | neg |
| | 2 | 1.97 | 2.3 | neg | neg | neg | neg |
| | 3 | 3.8 | 3.8 | 2.9 | 2.3 | neg | 2.0 |
| | 4 | 4.2 | 3.6 | 5.0 | 3.8 | 2.8 | 4.2 |
| | 7 | 5.0 | 4.5 | 4.8 | 5.6 | 2.6 | 5.8 |
| | 9 | 5 | 5.1 | 4.6 | 4.6 | 4.1 | 6.5 |

*neg: viral titers $\leq 1.8$ $TCID_{50}$/ml

Example 6

Immunization, Challenge, and Clinical Analysis

For protection studies, 12 pigs were randomly allocated into 3 groups of 4 animals each. Pigs in groups 1 and 2 were intranasally inoculated with NS4B-VGIv; pigs in group 3 were mock infected. At 3 DPI (group 1) or 28 DPI (group 2), animals were challenged with BICv along with animals in group 3. Clinical signs and body temperature were recorded daily throughout the experiment as described above. Blood, serum, nasal swabs and tonsil scrapings were collected at times post-challenge, with blood obtained from the anterior vena cava in EDTA-containing tubes (Vacutainer) for total and differential white blood cell counts. Total and differential white blood cell and platelet counts were obtained using a Beckman Coulter ACT (Beckman, Coulter, Calif.).

The limited in vivo replication kinetics of NS4B-VGIv is similar to that observed with CSICv (Risatti et al. 2005a, supra), a CSFV vaccine strain. However, restricted viral in vivo replication could also impair protection against wild-type virus infection. Thus, the ability of NS4B-VGIv to induce protection against virulent BICv was assessed in early and late vaccination-exposure experiments.

Mock-vaccinated control pig groups receiving BICv only (n=4) developed anorexia, depression, and fever by 4 days post-challenge (DPC), and a marked reduction of circulating leukocytes and platelets by 4 DPC (data not shown), and died or were euthanized in extremis by 10 DPC (Table 4). Notably, NS4B-VGIv induced complete protection by 3 and 28 DPI. All pigs survived infection and remained clinically normal, without significant changes in their hematological values (data not shown).

TABLE 4

Swine survival and fever response after challenge of NS4B-VGIv-infected animals with virulent BICv.

| | CSFV Symptoms | | Fever | |
|---|---|---|---|---|
| Vaccine/ Challenge Time | # Survivors/ Total # | Mean time to death (days ± SD) | Mean time to onset (days ± SD) | Duration (days ± SD) |
| NS4B.VGI/3DPI | 4/4 | No | — | — |
| NS4B.VGI/28DPI | 4/4 | No | No | No |
| Mock/BICv | 0/4 | Yes/10 (0) | 4.5 (0.7) | 9.5 (0.7) |

SD: Standard Deviation

Viremia and virus shedding of vaccinated-exposed animals were examined at 4, 6, 8, 14 and 21 DPC (Table 5). As expected, in mock-vaccinated control animals, viremia was observed by 4 DPC, with virus titers remaining high by 8 DPC (approximately $10^{7.8}$ $TCID_{50}$/ml) in the surviving pigs. Furthermore, virus was detected in nasal swabs and tonsil scrapings of these animals after 4-6 DPC. Conversely, presence of virus was not detected in any clinical sample obtained from pigs challenged either at 3 or 28 DPI. Even though NS4B-VGIv showed a limited in vivo growth, a solid protection was induced shortly after vaccination.

TABLE 5

Detection of virus in nasal swabs, tonsil scrapings, and blood samples obtained after challenge of NS4B-VGIv infected animals with virulent BICv.

| Challenge Group | Sample | C* | Days Post-Challenge | | | | | |
|---|---|---|---|---|---|---|---|---|
| | | | 4 | 6 | 8 | 12 | 14 | 21 |
| 3 DPI | Nasal | 0/4[a] | 0/4 | 0/4 | 0/4 | 0/4 | 0/4 | 0/4 |
| | Tonsil | 0/4 | 0/4 | 0/4 | 0/4 | 0/4 | 0/4 | 0/4 |
| | Blood | 0/4 | 0/4 | 0/4 | 0/4 | 0/4 | 0/4 | 0/4 |
| 28 DPI | Nasal | 0/4 | 0/4 | 0/4 | 0/4 | 0/4 | 0/4 | 0/4 |
| | Tonsil | 0/4 | 0/4 | 0/4 | 0/4 | 0/4 | 0/4 | 0/4 |
| | Blood | 0/4 | 0/4 | 0/4 | 0/4 | 0/4 | 0/4 | 0/4 |
| Control | Nasal | 0/2 | 0/2 | 2/2 (4.4) | 2/2 (4.9) | D | D | D |
| | Tonsil | 0/2 | 1/2 (2.0)[b] | 2/2 (4.1) | 2/2 (4.8) | D | D | D |
| | Blood | 0/3 | 2/2 (4.5) | 2/2 (7.4) | 2/2 (7.8) | D | D | D |

*C: Day of Challenge
[a] Number of animals positive for virus isolation over total number of challenged animals.
[b] Number in parentheses indicates average virus titers expressed as $\log_{10} TCID_{50}$/ml for four animals.
D Animals in this group were all dead by this time point.

In summary, we present here data demonstrating that a putative TLR motif in NS4B is important as a virulent determinant during the infection on pigs. Additionally, it is shown that animals infected with NS4B-VGIv were completely protected against virulent challenge with Brescia virus both at 3 and 28 days post-vaccination. Thus, VGIv serves as a candidate vaccine virus, displaying advantages over classic live attenuated strains since the molecular basis of its attenuation is known.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated polynucleotide molecule comprising a DNA sequence encoding an infectious RNA molecule that encodes a genetically modified classical swine fever virus (CSFV) mutant of a highly pathogenic native Brescia strain, wherein said CSFV mutant encodes a genetically modified non-structural glycoprotein B4 (NS4B) set forth in SEQ ID NO: 2 that comprises an altered toll-like receptor (TLR) such that when said genetically modified CSFV mutant infects a porcine animal, it is unable to produce a pathogenic CSFV infection in said animal.

2. The isolated polynucleotide molecule of claim 1, wherein said genetically modified NS4B gene has mutated amino acids valine, glycine, and isoleucine in positions 2566, 2567, and 2568 of the TLR motif to alanine, alanine, and alanine, respectively.

3. The isolated polynucleotide molecule of claim 1, wherein said DNA sequence is SEQ ID NO: 1 or a sequence fully complementary thereof, wherein said DNA sequence contains a mutation that alters the TLR motif of amino acids 2566-2568 of the encoded NS4B set forth in SEQ ID NO:2.

4. A method for generating a genetically modified CSFV, which method comprises transfecting a host cell with an infectious RNA molecule that encodes the genetically modified CSFV mutant according to claim 1 and obtaining the genetically modified CSFV mutant generated by the transfected host cell.

5. An isolated recombinant classical swine fever virus comprising the RNA molecule according to claim 1, said RNA sequence encodes a genetically modified NS4B protein.

6. A genetically modified CSFV mutant, wherein the CSFV is encoded by the isolated polynucleotide molecule of claim 1.

7. A vaccine for protecting a porcine animal against infection by a CSFV, which vaccine comprises:

(a) a genetically modified CSFV encoded by an infectious RNA molecule encoded by the polynucleotide molecule according to claim 1, or
(b) the infectious RNA molecule of claim 1, wherein the vaccine is in an effective amount to produce an immunoprotection against a CSF virus infection; and a carrier acceptable for veterinary use.

8. A CSF vaccine comprising a genetically modified CSFV mutant that does not produce CSF disease in swine, wherein said virus is encoded by the polynucleotide of claim 1.

9. A rationally designed live attenuated CSF vaccine comprising a recombinant classical swine fever virus according to claim 5.

10. A method of immunizing an animal against CSF, comprising administering to said animal a vaccine comprising the isolated recombinant CSF virus according to claim 5.

11. A method of protecting an animal against CSF, comprising administering to said animal an effective amount of the vaccine of claim 9 to protect said animal from a clinical CSF disease.

* * * * *

SEQUENCE LISTING

```
<160> NUMBER OF SEQ ID NOS: 4

<210> SEQ ID NO 1
<211> LENGTH: 12285
<212> TYPE: DNA
<213> ORGANISM: Classical swine fever virus

<400> SEQUENCE: 1
agttcattct cgtgtacatg attggacaaa tcaaaatctc aatttggttc agggcctccc      60
tccagcgacg gccgagctgg gctagccatg cccacagtag gactagcaaa cggagggact     120
agccgtagtg gcgagctccc tgggtggtct aagtcctgag tacaggacag tcgtcagtag     180
ttcgacgtga gcagaagccc acctcgagat gctatgtgga cgagggcatg cccaagacac     240
accttaaccc tagcggggt cgttagggtg aaatcacacc atgtgatggg agtacgacct      300
gatagggtgc tgcagaggcc cactattagg ctagtataaa aatctctgct gtacatggca     360
catggagttg aatcattttg aactttata caaaacaaac aaacaaaaac caatgggagt       420
ggaggaaccg gtatacgatg taacggggag accattgttt ggagacccaa gtgaggtaca     480
cccacaatca acattgaagc taccacatga taggggggaga ggcaacatca aaacaacact    540
gaagaaccta cctaggagag gtgactgcag gagtggcaac cacctaggcc cggttagtgg     600
gatatatgta aagcccggcc ctgtcttta tcaggactac atgggcccag tctatcatag      660
agcccctcta gagttttttg acgaagcaca gttttgtgag gtgaccaaaa ggataggtag     720
ggtgacaggt agtgacggaa agctttacca tatatacgtg tgcatcgatg gttgcatcct     780
gctgaagcta gccaagaggg gcgagccaag aaccctgaag tggattagaa atctcaccga     840
ctgtccattg tgggttacca gttgttctga tgatggtgca agtgcaagta aagagaagaa     900
accagatagg atcaacaagg gtaaattaaa gatagcccca aaagagcatg agaaggacag     960
caggactaag ccacctgatg ctacgattgt agtggaagga gtaaaatacc aggtcaaaaa    1020
```

```
gaaaggtaaa gttaagggaa agaatacccca agacggcctg taccacaaca agaataaacc    1080
accagaatct aggaagaaat tagaaaaagc cctattggca tgggcagtga tagcaattat    1140
gttataccaa cctgttgcag ccgaaaatat aactcaatgg aacctgagtg acaacggtac    1200
caatggtatc cagcacgcta tgtaccttag aggagtcagc agaagcttgc atgggatctg    1260
gccagaaaaa atatgcaaag gagtccccac ctacctggcc acagacacgg aactgagaga    1320
aatacaggga atgatggatg ccagcgaggg gacaaactat acgtgctgta agttacagag    1380
acatgaatgg aacaaacatg gatggtgtaa ctggtataac atagacccct ggatacagtt    1440
gatgaataga acccaagcaa acttggcaga aggccctccg agcaaggagt gcgccgtgac    1500
ttgcaggtac gataaaaatg ctgacattaa cgtggtcacc caggccagaa acaggccaac    1560
caccctaact ggctgcaaga aagggaaaaa tttttctttt gcgggtacag ttatagaggg    1620
cccatgtaat ttcaacgttt ctgttgagga tatcttatat ggggatcatg agtgtggcag    1680
tctactccag gatacggctc tatacctagt agatggaatg accaacacta tagagagagc    1740
caggcaggga gccgcgaggg tgacatcttg gctagggagg caactcagaa ctgccgggaa    1800
gaggttggag ggcagaagca aaacctggtt tggtgcctat gccctatcac cttattgtaa    1860
tgtgacaagc aaaatagggt acatatggta cactaacaac tgtaccccgg cttgcctccc    1920
caaaaataca aagataatag gccccggtaa atttgacact aacgcggaag acggaaagat    1980
tctccatgag atgggggggcc acctatcaga atttctgctg ctctctctgg tcgttctgtc    2040
tgacttcgcc cctgaaacag ccagcgcgtt atacctcatt ttgcactacg tgatccctca    2100
atcccatgaa gaacctgaag gctgtgacac aaaccagctg aatttaacag tggaactcag    2160
gactgaagac gtgataccat catcagtctg gaatgttggc aaatatgtgt gtgttagacc    2220
agactggtgg ccatatgaaa ccaaggtggc tttgttattt gaagaggcag acaggtcgt    2280 aaagttagcc ttgcgggcac tgagggattt aaccagggtc tggaatagcg catcaaccac    2340
ggcattcctc atctgcttga taaaagtatt aagaggacag gtcgtgcaag gtgtgatatg    2400
gctgttactg gtaactgggg cacaaggccg gctagcctgc aaggaagatc acaggtacgc    2460
tatatcaaca accaatgaga tagggctact tggggccgaa ggtctcacta ccacctggaa    2520
agaatacaac cacaatttgc aactggatga tgggaccgtc aaggccatct gcatggcagg    2580 ttccttttaaa gtcacagcac ttaatgtggt tagtaggagg tatctggcat cattacataa    2640
ggacgcttta cccacttccg tgacattcga gctcctgttc gacgggacca gcccattgac    2700
cgaggaaatg ggagatgact tcgggttcgg actgtgtccg tatgatacga gccctgtagt    2760
caagggaaag tacaacacaa ccttgttgaa tggtagtgca ttctacctag tttgcccaat    2820
agggtggacg ggtgttatag agtgcacggc agtgagcccg acaactctga acagaagt    2880 ggtaaagacc ttcagaagag agaaacccct tccgtacaga agggattgtg tgaccactac    2940
agtgaaaaat gaagatctat tctactgtaa atggggggc aattggacat gtgtgaaagg    3000
tgaaccagtg acctacacgg gggggccagt aaaacaatgc agatggtgtg gcttcgactt    3060
caatgagcct gacggactcc cacactaccc cataggtaag tgcattttgg caaatgagac    3120
aggttacaga atagtggatt caacggactg taacagagat ggcgttgtaa tcagcacaga    3180
ggggagtcat gagtgcttga ttggtaacac aactgtcaag gtgcatgcat tagatgaaag    3240
actaggccct atgccatgca ggcctaagga gatcgtctct agtgcgggac ctgtaaggaa    3300
aacttcctgt acattcaact acgcaaaaac tctgaggaac aggtattatg agcccaggga    3360
cagctatttc caacaatata tgctcaaggg cgagtatcag tactggtttg atctggatgt    3420
```

-continued

```
gaccgaccgc cactcagatt acttcgcaga attcattgtc ttggtggtgg tggcactgtt    3480
gggaggaaga tatgtcctgt ggctaatagt gacctacata gttctaacag aacaactcgc    3540
cgctggtcta cagttaggcc agggtgaggt agtgttaata gggaacttaa tcacccacac    3600
agatattgag gttgtagtat atttcttact gctctatttg gtcatgagag atgagcctat    3660
aaagaaatgg atactactgc tgttccatgc tatgaccaac aatccagtta agaccataac    3720
agtggcactg ctcatggtta gcggggttgc caagggtgga aagatagatg gtggttggca    3780
gcggctgccg gagaccaact ttgatatcca actcgcgctg acagttatag tagtcgctgt    3840
gatgttgctg gcaaagaaag atccgactac cgtccccttg gttataacgg tggcaaccct    3900
gagaacggct aagataacta atggacttag tacagatcta gccatagcta cagtgtcaac    3960
agctttgcta acctggacct acattagtga ctattataaa tacaagacct tgctacagta    4020
ccttattagc acagtgacag gtatcttctt gataagggta ctgaagggggg taggtgagtt    4080 agatttacac accccaacct taccatctta cagaccccctc ttcttcatcc tcgtgtacct    4140
catttccact gcagtggtaa caagatggaa tctggacata gccggattgc tgctgcagtg    4200
tgtcccaacc cttttaatgg ttttcacgat gtgggcagac atccttaccc tgatcctcat    4260
actgcctact tacgagttga caaaactata ttacctcaag gaagtgaaga ttggggcaga    4320
aaggggctgg ttgtggaaga ccaacttcaa gagggtaaat gacatatacg aagttgacca    4380
agctggtgag ggggtgtacc ttttcccatc aaaacaaaag acaggtacaa taacaggtac    4440
tatgttgcca ttgatcaaag ccatactcat aagttgcatc agcaataagt ggcaatttat    4500
atatctattg tacttgatat tcgaagtgtc ttactacctt cacaagaaga tcatagatga    4560
aatagcagga gggaccaact tcatctcgag acttgtagcc gctctgattg aagccaattg    4620
ggcctttgac aacgaagaag ttagaggttt aaagaagttc ttcctgctgt ctagtagggt    4680
taaagaactg atcatcaaac acaaagtgag gaatgaagtg atggtccact ggtttggcga    4740
cgaagaggtc tatgggatgc cgaagctggt tggcttagtc aaggcagcaa cactgagtaa    4800
aaataaacat tgtattttgt gcaccgtctg tgaaaacaga gagtggagag agaaacctg    4860 cccaaaatgc ggccgttttg gccaccagt gacctgtggc atgaccctag ccgactttga    4920
agaaaaacac tataagagga ttttctttag agaggatcaa tcagaagggc cggttaggga    4980
ggagtatgca gggtatctgc aatatagagc cagagggcaa ttattcctga ggaatctccc    5040
ggtgctagca acaaaagtca gatgctcct ggtcggaaat cttgggacgg aggtgggga    5100 tttggaacac cttggctggg tgctcagagg gcctgccgtt tgcaagaagg ttaccgaaca    5160
tgagaaatgc accacatcca taatggacaa attaactgct ttcttcggtg ttatgccaag    5220
gggcaccaca cctagagccc ctgtgagatt ccccacctct ctcttaaaga taagaagggg    5280
gctggaaact ggctgggcgt acacacacca aggtggcatc agttcagtgg accatgtcac    5340
ttgtgggaaa gacttactgg tatgtgacac tatgggccgg acaagggttg tttgccaatc    5400
aaataacaag atgacagacg agtccgagta tggagttaaa actgactccg gatgcccgga    5460
gggagctagg tgttacgtgt tcaacccaga ggcagttaac atatccggga ctaaaggagc    5520
catggtccac ttacaaaaaa ctggaggaga attcacctgt gtgacagcat cagggactcc    5580
ggccttcttt gatctcaaga acctcaaagg ctggtcaggg ctgccgatat ttgaggcatc    5640
aagtggaaga gtagtcggca gggttaaggt cgggaagaat gaggactcta aaccaaccaa    5700
gcttatgagt ggaatacaaa cagtctccaa agtaccaca gacttgacag aaatggtaaa    5760
gaaaataaca accatgaaca ggggagaatt cagacaaata acccttgcca caggtgccgg    5820
```

```
aaaaaccacg gaactcccta gatcagtcat agaagagata ggaaggcata agagggtctt    5880
ggtcttgatc cctctgaggg cggcagcaga gtcagtatac caatatatga gacaaaaaca    5940
cccaagcata gcattcaact tgaggatagg ggagatgaag gaaggggaca tggccacagg    6000
gataacctat gcctcatatg gttacttctg tcagatgcca caacctaagc tgcgagccgc    6060
gatggttgag tactccttca tattccttga tgagtaccac tgtgccaccc ccgaacaatt    6120
ggctatcatg ggaaagatcc acagattttc agagaacctg cgggtagtag ccatgaccgc    6180
aacaccagca ggcacggtaa caactacagg gcaaaaacac cctatagaag aatacatagc    6240
cccagaagtg atgaagggggg aagacttagg ttcagagtac ttggacatag ctggactaaa    6300
gataccagta gaggagatga agagtaacat gctggtcttt gtgcccacaa ggaacatggc    6360
tgtagagacg gcaaagaaac tgaaagctaa gggttataac tcaggctact attatagtgg    6420
agaggatcca tctaacctga gggtggtaac atcacagtcc ccgtacgtgg tggtagcaac    6480
caacgcaata gaatcaggtg ttactctccc agacttggat gtggtcgtcg acacagggct    6540
taagtgtgaa aagaggatac ggctgtcacc taagatgccc ttcatagtga cgggcctgaa    6600
gagaatggct gtcacgattg gggaacaagc ccagagaagg gggagagttg ggagagtgaa    6660
gcctgggaga tactacagga gtcaagaaac ccccgttggt tccaaagatt accattacga    6720
cctactgcaa gcacagaggt acggtataga agatgggata aacatcacca aatcttttag    6780
agagatgaat tatgattgga gcctttatga ggaggatagt ctgatgatta cacaattgga    6840
aatcctcaac aatctgttga tatcagaaga gctaccaatg gcagtaaaaa atataatggc    6900
caggactgac cacccagaac caatccaact ggcgtacaac agctacgaaa cgcaggtgcc    6960
agtgctattc ccaaaaataa aaatggaga ggtgactgac agttacgata actataccct    7020
cctcaacgca agaaagctgg gggatgatgt acctcccta gtgtatgcca cagaggatga    7080
ggacttagcg gtagagctgc tgggcttaga ctggccggac cctggaaacc aaggaaccgt    7140
ggaggctggt agagcactaa acaagtagt tggtctatca acagctgaga cgccctgtt    7200
agtagcttta ttcggctatg taggatatca ggcactctca aagaggcata taccagtagt    7260
cacagacata tattcaattg aagatcacag gttggaagac accacacacc tacagtatgc    7320
cccgaatgct atcaagacgg aggggaagga gacagaattg aaggagctag ctcaggggga    7380
tgtgcagaga tgtatggaag ctatgactaa ttatgcaaga gatggcatcc aattcatgaa    7440
gtctcaggca ctgaaagtga agaaacccc cacttacaaa gagacaatgg acaccgtggc    7500
ggactatgta aagaagttca tggaggcact ggcggacagc aaagaagaca tcataaaata    7560
tgggttgtgg gggacgcaca caaccttata taagagcatc ggtgctaggc ttgggaacga    7620
gactgcgttc gctaccctgg tcgtgaaatg gctggcatt gggggagaat caatagcaga    7680
ccatgtcaaa caagcggcca cagacttggt cgtttactat atcatcaaca gacctcagtt    7740
cccaggagac acggagacac aacaggaagg aaggaaattt gtagccagcc tactggtctc    7800
agccctggct acttacactt acaaaagctg gaattacaat aatctgtcca agatagttga    7860
accggctttg gctactctgc cctatgccgc cacagctctc aagctattcg ccccactcg    7920
attggagagc gttgtcatac tgagtaccgc aatctacaaa acctacctat caatcaggcg    7980
cggaaaaagc gatggttttgc taggcacagg ggttagtgcg gctatggaaa tcatgtcaca    8040
aaacccagta tctgcggctg cagcggtcat gctaggggtg ggggccgtag cggcccacaa    8100
tgcaatcgaa gccagtgagc agaagagaac actactcatg aaagtttttg taaagaactt    8160
cttggatcag gcagccactg atgaattagt caaggagagc cctgagaaaa taataatggc    8220
```

```
tttgtttgaa gcagtgcaga cagtcggcaa ccctcttaga ctggtatacc acctttacgg   8280
agttttttac aaagggtggg aggcaaaaga gttggcccaa aggacagccg gtaggaatct   8340
tttcactttg ataatgtttg aggctgtgga actactggga gtagatagcg aaggaaagat   8400
ccgccagcta tcaagcaatt acatactaga gctcctgtat aagttccgtg acagtatcaa   8460
gtccagcgtg aggcagatgg caatcagctg ggcccctgcc ccttttagtt gtgattggac   8520
accgacggat gacagaatag ggcttcccca agataatttc ctccgagtgg agacaaaatg   8580
cccctgtggt tacaagatga aagcagttaa gaattgtgct ggggagttga gactcttaga   8640
agaggaaggc tcatttctct gcaggaataa attcgggaga ggttcacgga actacagggt   8700
gacaaaatac tatgatgaca atctatcaga aataaagcca gtgataagaa tggaaggaca   8760
tgtggaactc tactacaagg gagccactat taaactggat ttcaacaaca gtaaaacaat   8820
attggcaacc gataaatggg aggtcgatca ctccactctg gtcagggtgc tcaagaggca   8880
cacaggggct ggatatcgtg gggcatacct gggtgagaaa ccgaaccaca acatctgat   8940 agagagggac tgcgcaacca tcaccaaaga taaggtttgt ttctcaaga tgaagagagg   9000 gtgtgcattt acttatgact tatcccttca caaccttacc cggctgatcg aattggtaca   9060
caagaataac ttgaagaca aagagattcc tgccgttacg gtcacaacct ggctggctta   9120
cacatttgta aatgaagata tagggaccat aaaaccagcc ttcggggaga aaataacacc   9180
agagatgcag gaggagataa ccttgcagcc tgctgtagtg gtggatgcaa ctgacgtgac   9240
cgtgaccgtg gtaggggaaa cccctactat gactacaggg gagacaccaa caacgttcac   9300
cagctcaggt ccagacccga aaggccaaca agttttaaaa ctgggagtag gtgaaggcca   9360 atacccggg actaatccac agagagcaag cctgcacgaa gccatacaaa gcgcagatga   9420
aaggccctct gtgttgatat tggggtctga taaagccacc tctaatagag tgaaaactgt   9480
aaagaatgtg aaggtataca gaggcaggga cccactagaa gtgagagata tgatgaggag   9540
gggaaagatc ctagtcatag ccctgtctag ggttgataat gctctattga aatttgtaga   9600
ttacaaaggc acctttctaa ctagagagac cctggaggca ttaagtttgg gtaggccaaa   9660
aaagaaaaac ataaccaagg cagaagcaca gtggttgctg cgcctcgaag accaaatgga   9720
agagctaccc gattggttcg cagccgggga acccattttt ttagaggcca atattaaaca   9780
tgacaggtat catctggtag gggatatagc tactatcaaa gagaaagcca acaattggg   9840 ggctacagac tctacaaaga tatccaagga ggttggtgca aaagtatatt ctatgaaatt   9900
gagtaattgg gtgatgcaag aagaaaacaa acagagcaac ttgacccct tatttgaaga   9960 gctcctacag cagtgtccac ccggaggcca aaacaaaact gcacatatgg tctctgctta  10020
ccaactagct caagggaact ggatgccaac cagctgccat gttttatgg ggaccatatc  10080 tgccagaagg actaagaccc atccatatga agcatatgtc aagttaaggg agttggtaga  10140
ggaacacaag atgaaaacat tgtgtcccgg atcaagtctg cgtaagcaca tgaatgggt  10200 aattggcaag atcaaatacc agggcaacct gaggaccaaa cacatgttga accccggcaa  10260
ggtggcagag caactgcaca gagaaggaca cagacacaat gtgtataaca agacaatagg  10320
ctcagtgatg acagctactg gcatcaggtt ggagaagttg cccgtggtta gggccagac  10380 agacacaacc aacttccacc aagcaataag ggataagata gacaaggaag gaatctaca  10440 gaccccgggt ttacataaga aactaatgga agttttcaat gcattgaaac gacccgagtt  10500
agagtcctcc tatgacgctg tggaatggga ggaattggag agaggaataa acagaaggg  10560 tgctgctggt ttcttgaac gcaaaaacat aggggagata ttggattcag agaaaaataa  10620
```

```
agtagaagag attattgaca atctgaaaaa gggtagaaat atcaaatact atgaaaccgc    10680
aatcccaaaa aatgaaaaga gggatgtcaa tgatgactgg accgcaggtg actttgtgga    10740
cgagaagaaa cccagagtca tacaatacce tgaagcaaaa acaaggctgg ccatcaccaa    10800
ggtgatgtat aagtgggtga agcagaagcc agtagtcata cccgggtatg aagggaagac    10860
acctctgttc caaattttg acaaagtaaa gaaggaatgg gatcaattcc aaaatccagt     10920
ggcagtgagc ttcgacacta aggcgtggga cacccaggtg accacaaatg atctggagct    10980
gataaaggac atacaaaagt actacttcaa gaagaaatgg cataaattta ttgacaccct    11040
gactatgcat atgtcagaag tacccgtaat cactgctgat ggggaggtgt atataaggaa    11100
agggcaaaga ggtagtggac agcccgacac aagcgcaggc aacagcatgc taaatgtgtt    11160
aacaatggtt tatgccttct gcgaggccac aggggtaccc tacaagagtt ttgacagggt    11220
ggcaaaaatt catgtgtgcg gggacgatgg tttcctgatc acagagagag ctctcggcga    11280
gaaattcgca agcaagggag tccaaatcct gtatgaagct gggaagcccc agaagatcac    11340
tgaaggggac aaaatgaaag tggcctacca atttgatgat attgagtttt gctcccatac    11400
accaatacaa gtaaggtggt cagataacac ttctagctac atgccaggga gaaatacaac    11460
cacaatcctg gctaaaatgg ccacaaggtt agattccagt ggtgagaggg gtaccatagc    11520
gtacgagaaa gcagtagcat tcagcttcct gctaatgtat tcctggaacc cactaatcag    11580
aaggatttgc ttattggtac tatcaactga actgcaagtg aaaccaggga agtcaaccac    11640
ttactattat gaaggggacc cgatatctgc ctacaaggaa gtcatcggcc acaatctttt    11700
cgatctcaag agaacaagct tcgagaagct ggccaagtta atctcagca tgtccgtact    11760 cggggcctgg actagacaca ccagcaaaag actactacaa gactgtgtca atatgggtgt    11820
taaagagggc aactggttag tcaatgcaga cagactggtg agtagtaaga ctggaaatag    11880
gtatgtacct ggagaaggcc acaccctgca agggagacat tatgaagaac tggtgttggc    11940
aagaaaacag atcaacagct tccaagggac agacaggtac aatctaggcc caatagtcaa    12000
catggtgtta aggaggctga gagtcatgat gatgaccctg ataggagag gggtatgagt    12060 gcgggtgacc cgcgatctgg acccgtcagt aggacctat tgtagataac actaatttt     12120 tattatta gatattacta tttatttat tatttattta ttgaatgagt aagaactggt      12180
acaaactacc tcatgttacc acactacact cattttaaca gcactttagc tggaaggaaa    12240
attcctgacg tccacagttg gactaaggta atttcctaac ggccc                    12285
```

<210> SEQ ID NO 2
<211> LENGTH: 3180
<212> TYPE: PRT
<213> ORGANISM: Classical swine fever virus

<400> SEQUENCE: 2

```
Met Glu Leu Asn His Phe Glu Leu Leu Tyr Lys Thr Asn Lys Gln Lys
1               5                   10                  15

Pro Met Gly Val Glu Glu Pro Val Tyr Asp Val Thr Gly Arg Pro Leu
            20                  25                  30

Phe Gly Asp Pro Ser Glu Val His Pro Gln Ser Thr Leu Lys Leu Pro
        35                  40                  45

His Asp Arg Gly Arg Gly Asn Ile Lys Thr Thr Leu Lys Asn Leu Pro
    50                  55                  60

Arg Arg Gly Asp Cys Arg Ser Gly Asn His Leu Gly Pro Val Ser Gly
65                  70                  75                  80

Ile Tyr Val Lys Pro Gly Pro Val Phe Tyr Gln Asp Tyr Met Gly Pro
```

```
                    85                  90                  95
Val Tyr His Arg Ala Pro Leu Glu Phe Phe Asp Glu Ala Gln Phe Cys
                100                 105                 110
Glu Val Thr Lys Arg Ile Gly Arg Val Thr Gly Ser Asp Gly Lys Leu
                115                 120                 125
Tyr His Ile Tyr Val Cys Ile Asp Gly Cys Ile Leu Leu Lys Leu Ala
                130                 135                 140
Lys Arg Gly Glu Pro Arg Thr Leu Lys Trp Ile Arg Asn Leu Thr Asp
145                 150                 155                 160
Cys Pro Leu Trp Val Thr Ser Cys Ser Asp Asp Gly Ala Ser Ala Ser
                165                 170                 175
Lys Glu Lys Lys Pro Asp Arg Ile Asn Lys Gly Lys Leu Lys Ile Ala
                180                 185                 190
Pro Lys Glu His Glu Lys Asp Ser Arg Thr Lys Pro Pro Asp Ala Thr
                195                 200                 205
Ile Val Val Glu Gly Val Lys Tyr Gln Val Lys Lys Gly Lys Val
                210                 215                 220
Lys Gly Lys Asn Thr Gln Asp Gly Leu Tyr His Asn Lys Asn Lys Pro
225                 230                 235                 240
Pro Glu Ser Arg Lys Lys Leu Glu Lys Ala Leu Leu Ala Trp Ala Val
                245                 250                 255
Ile Ala Ile Met Leu Tyr Gln Pro Val Ala Ala Glu Asn Ile Thr Gln
                260                 265                 270
Trp Asn Leu Ser Asp Asn Gly Thr Asn Gly Ile Gln His Ala Met Tyr
                275                 280                 285
Leu Arg Gly Val Ser Arg Ser Leu His Gly Ile Trp Pro Glu Lys Ile
                290                 295                 300
Cys Lys Gly Val Pro Thr Tyr Leu Ala Thr Asp Thr Glu Leu Arg Glu
305                 310                 315                 320
Ile Gln Gly Met Met Asp Ala Ser Glu Gly Thr Asn Tyr Thr Cys Cys
                325                 330                 335
Lys Leu Gln Arg His Glu Trp Asn Lys His Gly Trp Cys Asn Trp Tyr
                340                 345                 350
Asn Ile Asp Pro Trp Ile Gln Leu Met Asn Arg Thr Gln Ala Asn Leu
                355                 360                 365
Ala Glu Gly Pro Pro Ser Lys Glu Cys Ala Val Thr Cys Arg Tyr Asp
                370                 375                 380
Lys Asn Ala Asp Ile Asn Val Val Thr Gln Ala Arg Asn Arg Pro Thr
385                 390                 395                 400
Thr Leu Thr Gly Cys Lys Lys Gly Lys Asn Phe Ser Phe Ala Gly Thr
                405                 410                 415
Val Ile Glu Gly Pro Cys Asn Phe Asn Val Ser Val Glu Asp Ile Leu
                420                 425                 430
Tyr Gly Asp His Glu Cys Gly Ser Leu Leu Gln Asp Thr Ala Leu Tyr
                435                 440                 445
Leu Val Asp Gly Met Thr Asn Thr Ile Glu Arg Ala Arg Gln Gly Ala
450                 455                 460
Ala Arg Val Thr Ser Trp Leu Gly Arg Gln Leu Arg Thr Ala Gly Lys
465                 470                 475                 480
Arg Leu Glu Gly Arg Ser Lys Thr Trp Phe Gly Ala Tyr Ala Leu Ser
                485                 490                 495
Pro Tyr Cys Asn Val Thr Ser Lys Ile Gly Tyr Ile Trp Tyr Thr Asn
                500                 505                 510
```

-continued

```
Asn Cys Thr Pro Ala Cys Leu Pro Lys Asn Thr Lys Ile Ile Gly Pro
            515                 520                 525

Gly Lys Phe Asp Thr Asn Ala Glu Asp Gly Lys Ile Leu His Glu Met
        530                 535                 540

Gly Gly His Leu Ser Glu Phe Leu Leu Ser Leu Val Val Leu Ser
545                 550                 555                 560

Asp Phe Ala Pro Glu Thr Ala Ser Ala Leu Tyr Leu Ile Leu His Tyr
                565                 570                 575

Val Ile Pro Gln Ser His Glu Pro Glu Gly Cys Asp Thr Asn Gln
                580                 585                 590

Leu Asn Leu Thr Val Glu Leu Arg Thr Glu Asp Val Ile Pro Ser Ser
            595                 600                 605

Val Trp Asn Val Gly Lys Tyr Val Cys Val Arg Pro Asp Trp Trp Pro
            610                 615                 620

Tyr Glu Thr Lys Val Ala Leu Leu Phe Glu Glu Ala Gly Gln Val Val
625                 630                 635                 640

Lys Leu Ala Leu Arg Ala Leu Arg Asp Leu Thr Arg Val Trp Asn Ser
                645                 650                 655

Ala Ser Thr Thr Ala Phe Leu Ile Cys Leu Ile Lys Val Leu Arg Gly
                660                 665                 670

Gln Val Val Gln Gly Val Ile Trp Leu Leu Leu Val Thr Gly Ala Gln
            675                 680                 685

Gly Arg Leu Ala Cys Lys Glu Asp His Arg Tyr Ala Ile Ser Thr Thr
            690                 695                 700

Asn Glu Ile Gly Leu Leu Gly Ala Glu Gly Leu Thr Thr Thr Trp Lys
705                 710                 715                 720

Glu Tyr Asn His Asn Leu Gln Leu Asp Asp Gly Thr Val Lys Ala Ile
                725                 730                 735

Cys Met Ala Gly Ser Phe Lys Val Thr Ala Leu Asn Val Val Ser Arg
            740                 745                 750

Arg Tyr Leu Ala Ser Leu His Lys Asp Ala Leu Pro Thr Ser Val Thr
            755                 760                 765

Phe Glu Leu Leu Phe Asp Gly Thr Ser Pro Leu Thr Glu Glu Met Gly
            770                 775                 780

Asp Asp Phe Gly Phe Gly Leu Cys Pro Tyr Asp Thr Ser Pro Val Val
785                 790                 795                 800

Lys Gly Lys Tyr Asn Thr Thr Leu Leu Asn Gly Ser Ala Phe Tyr Leu
                805                 810                 815

Val Cys Pro Ile Gly Trp Thr Gly Val Ile Glu Cys Thr Ala Val Ser
            820                 825                 830

Pro Thr Thr Leu Arg Thr Glu Val Val Lys Thr Phe Arg Arg Glu Lys
            835                 840                 845

Pro Phe Pro Tyr Arg Arg Asp Cys Val Thr Thr Thr Val Glu Asn Glu
850                 855                 860

Asp Leu Phe Tyr Cys Lys Trp Gly Gly Asn Trp Thr Cys Val Lys Gly
865                 870                 875                 880

Glu Pro Val Thr Tyr Thr Gly Gly Pro Val Lys Gln Cys Arg Trp Cys
                885                 890                 895

Gly Phe Asp Phe Asn Glu Pro Asp Gly Leu Pro His Tyr Pro Ile Gly
            900                 905                 910

Lys Cys Ile Leu Ala Asn Glu Thr Gly Tyr Arg Ile Val Asp Ser Thr
            915                 920                 925

Asp Cys Asn Arg Asp Gly Val Val Ile Ser Thr Glu Gly Ser His Glu
930                 935                 940
```

-continued

Cys Leu Ile Gly Asn Thr Thr Val Lys Val His Ala Leu Asp Glu Arg
945                 950                 955                 960

Leu Gly Pro Met Pro Cys Arg Pro Lys Glu Ile Val Ser Ser Ala Gly
                965                 970                 975

Pro Val Arg Lys Thr Ser Cys Thr Phe Asn Tyr Ala Lys Thr Leu Arg
            980                 985                 990

Asn Arg Tyr Tyr Glu Pro Arg Asp Ser Tyr Phe Gln Gln Tyr Met Leu
        995                 1000                1005

Lys Gly Glu Tyr Gln Tyr Trp Phe Asp Leu Asp Val Thr Asp Arg
    1010                1015                1020

His Ser Asp Tyr Phe Ala Glu Phe Ile Val Leu Val Val Ala
    1025                1030                1035

Leu Leu Gly Gly Arg Tyr Val Leu Trp Leu Ile Val Thr Tyr Ile
    1040                1045                1050

Val Leu Thr Glu Gln Leu Ala Ala Gly Leu Gln Leu Gly Gln Gly
    1055                1060                1065

Glu Val Val Leu Ile Gly Asn Leu Ile Thr His Thr Asp Ile Glu
    1070                1075                1080

Val Val Val Tyr Phe Leu Leu Leu Tyr Leu Val Met Arg Asp Glu
    1085                1090                1095

Pro Ile Lys Lys Trp Ile Leu Leu Leu Phe His Ala Met Thr Asn
    1100                1105                1110

Asn Pro Val Lys Thr Ile Thr Val Ala Leu Leu Met Val Ser Gly
    1115                1120                1125

Val Ala Lys Gly Gly Lys Ile Asp Gly Gly Trp Gln Arg Leu Pro
    1130                1135                1140

Glu Thr Asn Phe Asp Ile Gln Leu Ala Leu Thr Val Ile Val Val
    1145                1150                1155

Ala Val Met Leu Leu Ala Lys Lys Asp Pro Thr Thr Val Pro Leu
    1160                1165                1170

Val Ile Thr Val Ala Thr Leu Arg Thr Ala Lys Ile Thr Asn Gly
    1175                1180                1185

Leu Ser Thr Asp Leu Ala Ile Ala Thr Val Ser Thr Ala Leu Leu
    1190                1195                1200

Thr Trp Thr Tyr Ile Ser Asp Tyr Tyr Lys Tyr Lys Thr Leu Leu
    1205                1210                1215

Gln Tyr Leu Ile Ser Thr Val Thr Gly Ile Phe Leu Ile Arg Val
    1220                1225                1230

Leu Lys Gly Val Gly Glu Leu Asp Leu His Thr Pro Thr Leu Pro
    1235                1240                1245

Ser Tyr Arg Pro Leu Phe Phe Ile Leu Val Tyr Leu Ile Ser Thr
    1250                1255                1260

Ala Val Val Thr Arg Trp Asn Leu Asp Ile Ala Gly Leu Leu Leu
    1265                1270                1275

Gln Cys Val Pro Thr Leu Met Val Phe Thr Met Trp Ala Asp
    1280                1285                1290

Ile Leu Thr Leu Ile Leu Ile Leu Pro Thr Tyr Glu Leu Thr Lys
    1295                1300                1305

Leu Tyr Tyr Leu Lys Glu Val Lys Ile Gly Ala Glu Arg Gly Trp
    1310                1315                1320

Leu Trp Lys Thr Asn Phe Lys Arg Val Asn Asp Ile Tyr Glu Val
    1325                1330                1335

Asp Gln Ala Gly Glu Gly Val Tyr Leu Phe Pro Ser Lys Gln Lys

```
            1340                1345                1350

Thr Gly Thr Ile Thr Gly Thr Met Leu Pro Leu Ile Lys Ala Ile
    1355                1360                1365

Leu Ile Ser Cys Ile Ser Asn Lys Trp Gln Phe Ile Tyr Leu Leu
    1370                1375                1380

Tyr Leu Ile Phe Glu Val Ser Tyr Tyr Leu His Lys Lys Ile Ile
    1385                1390                1395

Asp Glu Ile Ala Gly Gly Thr Asn Phe Ile Ser Arg Leu Val Ala
    1400                1405                1410

Ala Leu Ile Glu Ala Asn Trp Ala Phe Asp Asn Glu Glu Val Arg
    1415                1420                1425

Gly Leu Lys Lys Phe Phe Leu Leu Ser Ser Arg Val Lys Glu Leu
    1430                1435                1440

Ile Ile Lys His Lys Val Arg Asn Glu Val Met Val His Trp Phe
    1445                1450                1455

Gly Asp Glu Glu Val Tyr Gly Met Pro Lys Leu Val Gly Leu Val
    1460                1465                1470

Lys Ala Ala Thr Leu Ser Lys Asn Lys His Cys Ile Leu Cys Thr
    1475                1480                1485

Val Cys Glu Asn Arg Glu Trp Arg Gly Glu Thr Cys Pro Lys Cys
    1490                1495                1500

Gly Arg Phe Gly Pro Pro Val Thr Cys Gly Met Thr Leu Ala Asp
    1505                1510                1515

Phe Glu Glu Lys His Tyr Lys Arg Ile Phe Phe Arg Glu Asp Gln
    1520                1525                1530

Ser Glu Gly Pro Val Arg Glu Glu Tyr Ala Gly Tyr Leu Gln Tyr
    1535                1540                1545

Arg Ala Arg Gly Gln Leu Phe Leu Arg Asn Leu Pro Val Leu Ala
    1550                1555                1560

Thr Lys Val Lys Met Leu Leu Val Gly Asn Leu Gly Thr Glu Val
    1565                1570                1575

Gly Asp Leu Glu His Leu Gly Trp Val Leu Arg Gly Pro Ala Val
    1580                1585                1590

Cys Lys Lys Val Thr Glu His Glu Lys Cys Thr Thr Ser Ile Met
    1595                1600                1605

Asp Lys Leu Thr Ala Phe Phe Gly Val Met Pro Arg Gly Thr Thr
    1610                1615                1620

Pro Arg Ala Pro Val Arg Phe Pro Thr Ser Leu Leu Lys Ile Arg
    1625                1630                1635

Arg Gly Leu Glu Thr Gly Trp Ala Tyr Thr His Gln Gly Gly Ile
    1640                1645                1650

Ser Ser Val Asp His Val Thr Cys Gly Lys Asp Leu Leu Val Cys
    1655                1660                1665

Asp Thr Met Gly Arg Thr Arg Val Val Cys Gln Ser Asn Asn Lys
    1670                1675                1680

Met Thr Asp Glu Ser Glu Tyr Gly Val Lys Thr Asp Ser Gly Cys
    1685                1690                1695

Pro Glu Gly Ala Arg Cys Tyr Val Phe Asn Pro Glu Ala Val Asn
    1700                1705                1710

Ile Ser Gly Thr Lys Gly Ala Met Val His Leu Gln Lys Thr Gly
    1715                1720                1725

Gly Glu Phe Thr Cys Val Thr Ala Ser Gly Thr Pro Ala Phe Phe
    1730                1735                1740
```

-continued

Asp Leu Lys Asn Leu Lys Gly Trp Ser Gly Leu Pro Ile Phe Glu
1745                1750                1755

Ala Ser Ser Gly Arg Val Val Gly Arg Val Lys Val Gly Lys Asn
1760                1765                1770

Glu Asp Ser Lys Pro Thr Lys Leu Met Ser Gly Ile Gln Thr Val
1775                1780                1785

Ser Lys Ser Thr Thr Asp Leu Thr Glu Met Val Lys Lys Ile Thr
1790                1795                1800

Thr Met Asn Arg Gly Glu Phe Arg Gln Ile Thr Leu Ala Thr Gly
1805                1810                1815

Ala Gly Lys Thr Thr Glu Leu Pro Arg Ser Val Ile Glu Glu Ile
1820                1825                1830

Gly Arg His Lys Arg Val Leu Val Leu Ile Pro Leu Arg Ala Ala
1835                1840                1845

Ala Glu Ser Val Tyr Gln Tyr Met Arg Gln Lys His Pro Ser Ile
1850                1855                1860

Ala Phe Asn Leu Arg Ile Gly Glu Met Lys Glu Gly Asp Met Ala
1865                1870                1875

Thr Gly Ile Thr Tyr Ala Ser Tyr Gly Tyr Phe Cys Gln Met Pro
1880                1885                1890

Gln Pro Lys Leu Arg Ala Ala Met Val Glu Tyr Ser Phe Ile Phe
1895                1900                1905

Leu Asp Glu Tyr His Cys Ala Thr Pro Glu Gln Leu Ala Ile Met
1910                1915                1920

Gly Lys Ile His Arg Phe Ser Glu Asn Leu Arg Val Val Ala Met
1925                1930                1935

Thr Ala Thr Pro Ala Gly Thr Val Thr Thr Thr Gly Gln Lys His
1940                1945                1950

Pro Ile Glu Glu Tyr Ile Ala Pro Glu Val Met Lys Gly Glu Asp
1955                1960                1965

Leu Gly Ser Glu Tyr Leu Asp Ile Ala Gly Leu Lys Ile Pro Val
1970                1975                1980

Glu Glu Met Lys Ser Asn Met Leu Val Phe Val Pro Thr Arg Asn
1985                1990                1995

Met Ala Val Glu Thr Ala Lys Lys Leu Lys Ala Lys Gly Tyr Asn
2000                2005                2010

Ser Gly Tyr Tyr Tyr Ser Gly Glu Asp Pro Ser Asn Leu Arg Val
2015                2020                2025

Val Thr Ser Gln Ser Pro Tyr Val Val Val Ala Thr Asn Ala Ile
2030                2035                2040

Glu Ser Gly Val Thr Leu Pro Asp Leu Asp Val Val Val Asp Thr
2045                2050                2055

Gly Leu Lys Cys Glu Lys Arg Ile Arg Leu Ser Pro Lys Met Pro
2060                2065                2070

Phe Ile Val Thr Gly Leu Lys Arg Met Ala Val Thr Ile Gly Glu
2075                2080                2085

Gln Ala Gln Arg Arg Gly Arg Val Gly Arg Val Lys Pro Gly Arg
2090                2095                2100

Tyr Tyr Arg Ser Gln Glu Thr Pro Val Gly Ser Lys Asp Tyr His
2105                2110                2115

Tyr Asp Leu Leu Gln Ala Gln Arg Tyr Gly Ile Glu Asp Gly Ile
2120                2125                2130

Asn Ile Thr Lys Ser Phe Arg Glu Met Asn Tyr Asp Trp Ser Leu
2135                2140                2145

-continued

| | | | | | | | | | | |
|---|---|---|---|---|---|---|---|---|---|---|
|Tyr|Glu 2150|Glu|Asp|Ser|Leu 2155|Met|Ile|Thr|Gln 2160|Leu Glu Ile Leu Asn|

Tyr Glu Glu Asp Ser Leu Met Ile Thr Gln Leu Glu Ile Leu Asn
    2150                2155            2160

Asn Leu Leu Ile Ser Glu Glu Leu Pro Met Ala Val Lys Asn Ile
    2165                2170            2175

Met Ala Arg Thr Asp His Pro Glu Pro Ile Gln Leu Ala Tyr Asn
    2180                2185            2190

Ser Tyr Glu Thr Gln Val Pro Val Leu Phe Pro Lys Ile Lys Asn
    2195                2200            2205

Gly Glu Val Thr Asp Ser Tyr Asp Asn Tyr Thr Phe Leu Asn Ala
    2210                2215            2220

Arg Lys Leu Gly Asp Asp Val Pro Pro Tyr Val Tyr Ala Thr Glu
    2225                2230            2235

Asp Glu Asp Leu Ala Val Glu Leu Leu Gly Leu Asp Trp Pro Asp
    2240                2245            2250

Pro Gly Asn Gln Gly Thr Val Glu Ala Gly Arg Ala Leu Lys Gln
    2255                2260            2265

Val Val Gly Leu Ser Thr Ala Glu Asn Ala Leu Leu Val Ala Leu
    2270                2275            2280

Phe Gly Tyr Val Gly Tyr Gln Ala Leu Ser Lys Arg His Ile Pro
    2285                2290            2295

Val Val Thr Asp Ile Tyr Ser Ile Glu Asp His Arg Leu Glu Asp
    2300                2305            2310

Thr Thr His Leu Gln Tyr Ala Pro Asn Ala Ile Lys Thr Glu Gly
    2315                2320            2325

Lys Glu Thr Glu Leu Lys Glu Leu Ala Gln Gly Asp Val Gln Arg
    2330                2335            2340

Cys Met Glu Ala Met Thr Asn Tyr Ala Arg Asp Gly Ile Gln Phe
    2345                2350            2355

Met Lys Ser Gln Ala Leu Lys Val Lys Glu Thr Pro Thr Tyr Lys
    2360                2365            2370

Glu Thr Met Asp Thr Val Ala Asp Tyr Val Lys Lys Phe Met Glu
    2375                2380            2385

Ala Leu Ala Asp Ser Lys Glu Asp Ile Ile Lys Tyr Gly Leu Trp
    2390                2395            2400

Gly Thr His Thr Thr Leu Tyr Lys Ser Ile Gly Ala Arg Leu Gly
    2405                2410            2415

Asn Glu Thr Ala Phe Ala Thr Leu Val Val Lys Trp Leu Ala Phe
    2420                2425            2430

Gly Gly Glu Ser Ile Ala Asp His Val Lys Gln Ala Ala Thr Asp
    2435                2440            2445

Leu Val Val Tyr Tyr Ile Ile Asn Arg Pro Gln Phe Pro Gly Asp
    2450                2455            2460

Thr Glu Thr Gln Gln Glu Gly Arg Lys Phe Val Ala Ser Leu Leu
    2465                2470            2475

Val Ser Ala Leu Ala Thr Tyr Thr Tyr Lys Ser Trp Asn Tyr Asn
    2480                2485            2490

Asn Leu Ser Lys Ile Val Glu Pro Ala Leu Ala Thr Leu Pro Tyr
    2495                2500            2505

Ala Ala Thr Ala Leu Lys Leu Phe Ala Pro Thr Arg Leu Glu Ser
    2510                2515            2520

Val Val Ile Leu Ser Thr Ala Ile Tyr Lys Thr Tyr Leu Ser Ile
    2525                2530            2535

Arg Arg Gly Lys Ser Asp Gly Leu Leu Gly Thr Gly Val Ser Ala

|      |      |      |      | 2540 |      |      |      |      | 2545 |      |      |      |      | 2550 |
|------|------|------|------|------|------|------|------|------|------|------|------|------|------|------|

Ala Met Glu Ile Met Ser Gln Asn Pro Val Ser Ala Ala Ala Ala
2555                     2560                    2565

Val Met Leu Gly Val Gly Ala Val Ala Ala His Asn Ala Ile Glu
2570                     2575                    2580

Ala Ser Glu Gln Lys Arg Thr Leu Leu Met Lys Val Phe Val Lys
2585                     2590                    2595

Asn Phe Leu Asp Gln Ala Ala Thr Asp Glu Leu Val Lys Glu Ser
2600                     2605                    2610

Pro Glu Lys Ile Ile Met Ala Leu Phe Glu Ala Val Gln Thr Val
2615                     2620                    2625

Gly Asn Pro Leu Arg Leu Val Tyr His Leu Tyr Gly Val Phe Tyr
2630                     2635                    2640

Lys Gly Trp Glu Ala Lys Glu Leu Ala Gln Arg Thr Ala Gly Arg
2645                     2650                    2655

Asn Leu Phe Thr Leu Ile Met Phe Glu Ala Val Glu Leu Leu Gly
2660                     2665                    2670

Val Asp Ser Glu Gly Lys Ile Arg Gln Leu Ser Ser Asn Tyr Ile
2675                     2680                    2685

Leu Glu Leu Leu Tyr Lys Phe Arg Asp Ser Ile Lys Ser Ser Val
2690                     2695                    2700

Arg Gln Met Ala Ile Ser Trp Ala Pro Ala Pro Phe Ser Cys Asp
2705                     2710                    2715

Trp Thr Pro Thr Asp Asp Arg Ile Gly Leu Pro Gln Asp Asn Phe
2720                     2725                    2730

Leu Arg Val Glu Thr Lys Cys Pro Cys Gly Tyr Lys Met Lys Ala
2735                     2740                    2745

Val Lys Asn Cys Ala Gly Glu Leu Arg Leu Leu Glu Glu Glu Gly
2750                     2755                    2760

Ser Phe Leu Cys Arg Asn Lys Phe Gly Arg Gly Ser Arg Asn Tyr
2765                     2770                    2775

Arg Val Thr Lys Tyr Tyr Asp Asp Asn Leu Ser Glu Ile Lys Pro
2780                     2785                    2790

Val Ile Arg Met Glu Gly His Val Glu Leu Tyr Tyr Lys Gly Ala
2795                     2800                    2805

Thr Ile Lys Leu Asp Phe Asn Asn Ser Lys Thr Ile Leu Ala Thr
2810                     2815                    2820

Asp Lys Trp Glu Val Asp His Ser Thr Leu Val Arg Val Leu Lys
2825                     2830                    2835

Arg His Thr Gly Ala Gly Tyr Arg Gly Ala Tyr Leu Gly Glu Lys
2840                     2845                    2850

Pro Asn His Lys His Leu Ile Glu Arg Asp Cys Ala Thr Ile Thr
2855                     2860                    2865

Lys Asp Lys Val Cys Phe Leu Lys Met Lys Arg Gly Cys Ala Phe
2870                     2875                    2880

Thr Tyr Asp Leu Ser Leu His Asn Leu Thr Arg Leu Ile Glu Leu
2885                     2890                    2895

Val His Lys Asn Asn Leu Glu Asp Lys Glu Ile Pro Ala Val Thr
2900                     2905                    2910

Val Thr Thr Trp Leu Ala Tyr Thr Phe Val Asn Glu Asp Ile Gly
2915                     2920                    2925

Thr Ile Lys Pro Ala Phe Gly Glu Lys Ile Thr Pro Glu Met Gln
2930                     2935                    2940

| | | | | | | | | | | |
|---|---|---|---|---|---|---|---|---|---|---|
| Glu | Glu | Ile | Thr | Leu | Gln | Pro | Ala | Val | Val | Asp | Ala Thr Asp |
| | 2945 | | | | 2950 | | | | 2955 | | |
| Val | Thr | Val | Thr | Val | Val | Gly | Glu | Thr | Pro | Thr | Met Thr Thr Gly |
| | 2960 | | | | 2965 | | | | 2970 | | |
| Glu | Thr | Pro | Thr | Thr | Phe | Thr | Ser | Ser | Gly | Pro | Asp Pro Lys Gly |
| | 2975 | | | | 2980 | | | | 2985 | | |
| Gln | Gln | Val | Leu | Lys | Leu | Gly | Val | Gly | Glu | Gly | Gln Tyr Pro Gly |
| | 2990 | | | | 2995 | | | | 3000 | | |
| Thr | Asn | Pro | Gln | Arg | Ala | Ser | Leu | His | Glu | Ala | Ile Gln Ser Ala |
| | 3005 | | | | 3010 | | | | 3015 | | |
| Asp | Glu | Arg | Pro | Ser | Val | Leu | Ile | Leu | Gly | Ser | Asp Lys Ala Thr |
| | 3020 | | | | 3025 | | | | 3030 | | |
| Ser | Asn | Arg | Val | Lys | Thr | Val | Lys | Asn | Val | Lys | Val Tyr Arg Gly |
| | 3035 | | | | 3040 | | | | 3045 | | |
| Arg | Asp | Pro | Leu | Glu | Val | Arg | Asp | Met | Met | Arg | Arg Gly Lys Ile |
| | 3050 | | | | 3055 | | | | 3060 | | |
| Leu | Val | Ile | Ala | Leu | Ser | Arg | Val | Asp | Asn | Ala | Leu Leu Lys Phe |
| | 3065 | | | | 3070 | | | | 3075 | | |
| Val | Asp | Tyr | Lys | Gly | Thr | Phe | Leu | Thr | Arg | Glu | Thr Leu Glu Ala |
| | 3080 | | | | 3085 | | | | 3090 | | |
| Leu | Ser | Leu | Gly | Arg | Pro | Lys | Lys | Lys | Asn | Ile | Thr Lys Ala Glu |
| | 3095 | | | | 3100 | | | | 3105 | | |
| Ala | Gln | Trp | Leu | Leu | Arg | Leu | Glu | Asp | Gln | Met | Glu Glu Leu Pro |
| | 3110 | | | | 3115 | | | | 3120 | | |
| Asp | Trp | Phe | Ala | Ala | Gly | Glu | Pro | Ile | Phe | Leu | Glu Ala Asn Ile |
| | 3125 | | | | 3130 | | | | 3135 | | |
| Lys | His | Asp | Arg | Tyr | His | Leu | Val | Gly | Asp | Ile | Ala Thr Ile Lys |
| | 3140 | | | | 3145 | | | | 3150 | | |
| Glu | Lys | Ala | Lys | Gln | Leu | Gly | Ala | Thr | Asp | Ser | Thr Lys Ile Ser |
| | 3155 | | | | 3160 | | | | 3165 | | |
| Lys | Glu | Val | Gly | Ala | Lys | Val | Tyr | Ser | Met | Lys | Leu |
| | 3170 | | | | 3175 | | | | 3180 | | |

```
<210> SEQ ID NO 3
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 3
gtcatactga gtaccgcagc cgccgcaacc tacctatcaa tcagg          45

<210> SEQ ID NO 4
<211> LENGTH: 45
<212> TYPE: DNA
<213> ORGANISM: Artificial Sequence
<220> FEATURE:
<223> OTHER INFORMATION: Chemically Synthesized

<400> SEQUENCE: 4
tcacaaaacc cagtatctgc ggctgcagcg gtcatgctag gggtg          45
```